United States Patent [19]

Bentley et al.

[11] 3,996,235

[45] Dec. 7, 1976

[54] 6-ISOCYANATO-6-SUBSTITUTED PENICILLINS

[75] Inventors: Peter Hubert Bentley, Rudgwick; John Peter Clayton, Horsham, both of England

[73] Assignee: Beecham Group Limited, Great Britain

[22] Filed: Apr. 10, 1975

[21] Appl. No.: 566,695

Related U.S. Application Data

[62] Division of Ser. No. 443,724, Feb. 19, 1974, Pat. No. 3,936,446.

[52] U.S. Cl. .................. 260/306.7 C; 260/239.1
[51] Int. Cl.² ............................... C07D 499/00
[58] Field of Search .................. 260/239.1, 306.7 C

[56] References Cited

UNITED STATES PATENTS 3,855,233   12/1974   Dolfini .......................... 260/239.1

OTHER PUBLICATIONS

German Offenlegungsschrift No. 2,337,105 (31 Jan. 1974).
Burger, Medicinal Chemistry (2nd Ed.) pp. 77-78 (1960).

*Primary Examiner*—Gerald A. Schwartz

[57] ABSTRACT

Intermediates useful in the preparation of compounds having a penam or cephem ring structure, particularly penicillins and cephalosporins, and their preparation.

5 Claims, No Drawings

6-ISOCYANATO-6-SUBSTITUTED PENICILLINS

This is a division of application Ser. No. 443,724 filed Feb. 19, 1974 now U.S. Pat. No. 3,936,446.

This invention relates to intermediates useful in the preparation of compounds having the penam or cephem ring structure particularly penicillin and cephalosporin compounds which have antibacterial activity.

According to the present invention there is provided a compound of formula (I)

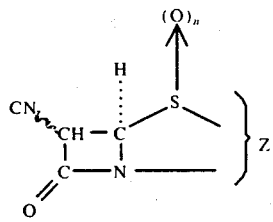

wherein n is 0 or 1 and Z is a divalent radical of formula (II), (III) or (IV)

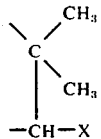 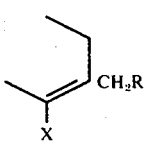 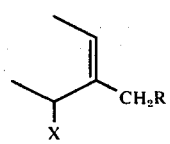

(II)    (III)    (IV)

wherein R is hydrogen an acetoxy group, a pyridinium group or a heterocyclic thio group, and X is a carboxylic acid group or a salt or ester derivative thereof or X and R taken together in formula (III) or (IV) represent the divalent radical

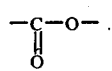

When X is an esterified carboxylic acid group, the most versatile esters are those which can readily be hydrolysed to the parent acid. Examples of suitable esters include the benzyl, para-methoxybenzyl, 2,2,2-trichloroethyl, and tert-butyl esters. Other suitable esters include the acyloxymethyl esters such as acetoxymethyl and pivaloyloxymethyl esters as well as "lactone" esters of structure (V)

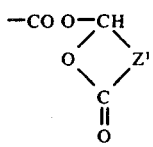

wherein $Z^1$ is a divalent radical such as 1,2-phenylene or 4,5-dimethoxyphenyl-1,2-ene-radical.

The CN—C bond in compound (I) may be either cis or trans with respect to the bridgehead hydrogen, and, as will be apparent later, mixtures of the cis and trans isomers are generally formed when preparing compounds (I).

When R is a heterocyclic thio group, particular examples include the following:

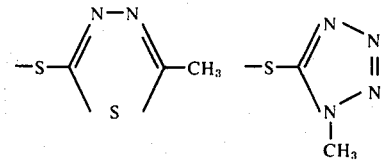

although many other examples of heterocyclic thio groups are known (see for example those listed in British Patent specification No. 1,328,340)

Compounds of formula (I) are prepared by reacting a compound of formula (VI)

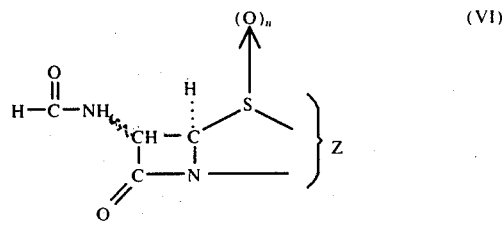

wehrein n and Z are as defined in formula (I) with phosgene in the presence of an acid acceptor. Preferably the acid acceptor is a tertiary amine such as N-methylmorpholine. The compound of formula (VI) used as starting material may be prepared by N-acylating the 6- or 7- amino compounds with an N-acylating derivative of formic acid e.g. formic-acetic anhydride or the intermediate formed when a carbodiimide coupling agent is used with formic-acid. The above reaction is most preferably carried out using a compound (VI) in which the group X is an esterified carboxylic acid group, since this gives a cleaner reaction. If desired, the ester group may then be hydrolysed to give the parent acid or salt. When cephem structures (I) are to be prepared, it may be preferable to carry out the phosgene reaction using a compound (VI) wherein R is not the ultimately desired group, and thereafter introduce the desired group e.g. by nucleophilic displacement. Thus the phosgene reaction might be carried out using the corresponding 3-acetoxy compound which is later displaced by a heterocyclic thiol.

In general, mixtures of the α- and β- isomers of the isocyano compound (I) are obtained after the phsogene reaction, the ratio of one isomer to the other being dependant on conditions such as solvent, temperature and time. Usually separation of isomers is not necessary since the isomeric mixture can be used as the intermediate in the same way as the pure isomers.

The valve of compounds (I) derives from their use in the preparation of the corresponding 6- or 7- substituted compound (VII)

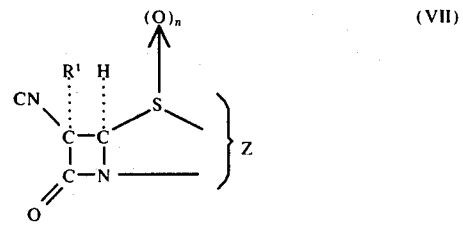

wherein $n$ and Z are as defined in formula (I) and $R^1$ is a group derived from an electrophile e.g. hydroxy alkyl, alkoxycarbonylalkyl, aralkoxycarbonylalkyl, aralkyl, alkylthio and the like. It is known that penicillins and cephalosporins having both an acylamino substituent and a second substituent at position 6- or 7- respectively are of value as antibacterial agents (cf Belgian Pat. No. 768,528). The isocyano group of compounds (VII) above may be converted to a free amino group by reaction with an acid which does not cleave the $\beta$-lactam ring of the penam or cephem (e.g. arylsulphonic acids such as p-toluenesulphonic acid). The free amino group may then be acylated by any of the N-acylation procedures known for semisynthetic penicillins and cephalosporins. In addition, the substituent $R^1$ in compounds (VII) may be modified further either before or after conversion of the isocyano group to an amino or acylamino group. Thus the versatility of the intermediate compounds (I) is clear, and specific examples of their use are given later in this specification.

The following Examples 1 to 9 illustrate the preparation of representative compounds of formula (I), whilst the remaining Examples illustrate the use of such compounds in the preparation of penam and cephem structures having an electrophile - derived substituent at position 6- or 7-.

EXAMPLE 1

Benzyl 6- Isocyanopenicillanate

A solution of benzyl 6$\beta$-formylaminopenicillanate (4g) in dry methylene chloride (40 ml) was treated with N-methylmorpholine (3.3 ml) and then at $-50°$ C with a methylene chloride solution of phosgene (1.2g). The reaction was exothermic. After 30 minutes at $-40°$ C ice-water was added and the organic phase was washed with water and dried. Evaporation gave crude benzyl 6-isocyanopenicillanate Column chromatography on silica gel using 30% v/v ethyl acetate in light petrol (60°–80° C) gave a semisolid mixture of the 6$\alpha$- and 6$\beta$- epimers (ratio 55:45) (1.2g), from which the 6$\alpha$- isomer was obtained by fractional crystallisation from ether, m p 87°–89° C. $\gamma_{N \equiv C}^{CHCl_3}$ 2140 cm$^{-1}$.

EXAMPLE 2

Following the same procedure as in Example 1, the phthalidyl ester of 6$\beta$- formylaminopenicillanic acid was converted to phthalidyl 6-isocyanopenicillanate. $\gamma_{max}$ (CHCl$_3$) 2120, 1790, 1770 (shoulder) cm$^{-1}$.

EXAMPLE 3

Following the same procedure as in Example 1, the t-butyl ester of 7$\beta$- formylaminocephalosporinate was converted to t-butyl 7$\beta$-isocyanocephalosporinate as a chromatographically homogeneous syrup $\gamma_{N \equiv C}^{CHCl_3}$ 2140 cm$^{-1}$.

EXAMPLE 4

A solution of methyl 7$\beta$- formylaminodesacetoxycephalosporanate (1.02g) in methylene chloride (25mls) was treated with N-methylmorpholine (1.1ml) and then at $-40°$ to $-50°$ C with a 2M solution of phosgene in methylene chloride (2.5 mls). After 1 hour, water was added and the organic phase separated. The latter was washed with aqueous sodium bicarbonate solution then with water, and dried and evaporated to give methyl - 7$\beta$-isocyanodesacetoxycephalosporanate. Chromatography on silica gel gave the product as an oil $\gamma_{max}$ (CH Cl$_3$) 2110 1785, 1720 cm$^{-1}$.

EXAMPLE 5

A solution of methyl 7$\beta$-formylamino -3-(2$^1$-methyl-1$^1$,3$^1$,4$^1$-thiadazol-5$^1$-yl)-thiomethylceph-3-em-4-carboxylate (0.81 g) in methylene chloride (15 mls) was treated with N-methylmorphine (0.56 ml) and then 4 $-50°$ to $-60°$ C with a 2M solution of phosgene in methylene chloride (1.2 mls). After 1 hour at $-40°$ C and 0.5 hour at 20° C ice-water was added and the organic layer separated. The latter was washed with aqueous sodium bicarbonate solution then water, and dried and evaporated. Chromatography on silica gave methyl 7$\beta$-isocyano-3-(2$^1$-methyl-1$^1$,3$^1$,4$^1$-thiadazol-5$^1$-yl)-thiomethylceph-3-em-4carboxylate. (0.16g) $\gamma_{max}$ (CH Cl$_3$) 2110, 1780, 1720 cm$^{-1}$.

EXAMPLE 6

By the general procedure of Example 1, using as starting material benzyl 6$\beta$- formylaminopenicillanate sulphoxide, benzyl 6-isocyanopenicillanate sulphoxide is prepared.

EXAMPLE 7

By the general procedure of Example 4 using as starting material methyl 7$\beta$-formylaminodesacetoxycephalosporanate, methyl 7$\beta$-formylaminodesacetoxycephalosporanate sulphoxide is prepared.

EXAMPLE 8

By the general procedure of Example 4 using as starting material methyl 7$\beta$-formylamino-3-methylceph-2-em-4-carboxylate, methyl 7$\beta$-isocyano-3-methylceph-2-em-4-carboxylate is prepared.

EXAMPLE 9

Catalytic hydrogenatation of the product of Example 1 using Raney Nickle produces 6-isocyanopenicillanic acid.

EXAMPLE 10

Benzyl 6$\alpha$-[1$'$-hydroxyisopropyl]-6$\beta$-isocyanaopenicillanate

A mixture of benzyl 6$\alpha$- and 6$\beta$-isocyanopenicillanate (0.71 g) dry acetone (5 ml.) and powdered potassium carbonate (0.31 g.) was stirred at 20° C with monitoring of the reaction by thin layer chromatography When all starting material had disappeared (2 hours) ice-water was added and the acetone was removed at 20° C. Extraction of the aqueous residue with ether was followed by washing the extracts with water drying and evaporation to yield the crude 6$\alpha$-[1$'$-hydroxyisopropyl] derivative. Purification by column chromatography on silica gel led to the product as a syrup (0.5 g.); $\gamma_{N \equiv C}^{CHCl_3}$ 2130 cm$^{-1}$.

EXAMPLE 11

Benzyl 6$\alpha$-methoxycarbonylmethyl-6$\beta$-isocyanopenicillanate

When a mixture of benzyl 6$\alpha$- and 6$\beta$-isocyanopenicillanate epimers, dimethylformamide (3 ml) and powdered potassium carbonate (0.24 g) were stirred together in the presence of methyl bromacetate (0.16 ml.) for 3 hours in an ice-bath, work up and chromatography as described in Example 10 led to the benzyl 6$\alpha$-methoxycorbonylmethyl-6$\beta$-isocyanopenicillanate as a clear colourless syrup, (0.3 g.); $\gamma_{max}^{CHCl_3}$ 2130, 1790, 1740 cm$^{-1}$.

EXAMPLE 12

Benzyl 6α-benzyloxycarbonylethyl-6β-isocyanopenicillanate

A mixture of benzyl 6α- and 6β-isocyanopenicillanate epimers (3.8 g) in dry dimethylformamide (15 ml.) was stirred at 20° C with powdered potassium carbonate (1.7 g) and benzyl acrylate (2.5 g.) for 1½ hours. Addition of ice-water was followed by extraction of the precipitated oil into ethyl acetate. The extracts were washed with water dried and evaporated. Column chromatography of the residue on silica gel using 30% ethyl acetate in petrol as eluent provided benzyl 6α-benzyloxycarbonylethyl-6β-isocyanopenicillanate as a syrup (2.8 g.); $\gamma_{N\equiv C}^{CHCl_3}$ 2120 cm$^{-1}$.

EXAMPLE 13

Benzyl 6α-benzyl-6β-isocyanopenicillanate

A mixture benzyl 6α- and 6β-isocyanopenicillanate epimers (1.0 g.) dimethylformamide (3.5 ml.), potassium carbonate (0.47 g.) and benzyl bromide (0 43 ml.) were stirred together for 2½ hours in an ice-bath. The reaction was worked up as in Example 10 and column chromatography gave benzyl 6α-benzyl-6β-isocyanopenicillanate (0.24 g.) m.p. 105°–7° C.

EXAMPLE 14 t-Butyl 7α-benzyloxycarbonylethyl-7β-isocyanocephalosporanate t-Butyl 6β-isocyanocephalosporanate was reacted as described in Example 12, chromatography of the crude product led to t-butyl 7α-benzyloxycarbonylethyl-7β-isocyanocepholosporanate as a colourless syrup; $\gamma_{max}^{CHCl_3}$ 2120, 1795, 1735 cm$^{-1}$.

EXAMPLE 15

Benzyl 6α-benzoylmethyl-6β-isocyanopenicillanate

A solution of benzyl 6-isocyanopenicillanate (mixed C6-epimers) (1.43g) in dimethylformamide containing anhydrous potassium carbonate (0.63g) and phenacylbromide (0.9 g) was stirred for 4 hours at 5° C. Work up and chromatography provided the desired compound as an oil (0.35 g.) $\gamma_{max}$ (CHCl$_3$): 2120, 1795, 1740, 1680 cm$^{-1}$.

EXAMPLE 16 t-butyl 7α-isocyano17β-methylthiocephalosporante

A mixture of 7β-isocyanocephalosporanate (1.7g), potassium carbonate (0.7g), methylmethoxycarbonyldisulphide (0 7 g.) and dimethylformamide (10 mls.) was stirred for 2¼ hours at 5°–10° C. After addition of water, the neutral product was isolated from ethylacetate. On the basis of spectral evidence this contained the desired isocyanide: $\gamma_{max}$(CHCl$_3$): 2120, 1795, 1740 cm$^{-1}$.

EXAMPLE 17

Benzyl 6α-benzyl-6β-aminopenicillanate

A solution of benzyl 6α-benzyl6β-isocyanopenicillanate (1.75g) in chloroform (50ml) was stirred with p-toluene sulphonic acid (0.83g) for ½ hour at 20°.

The chloroform was washed with aq. sodium bicarbonate, dried and evaporated to give the essentially pure amine (100%). Chromatography over silica gel provided the pure amine, m.p. 99°–101°$\gamma_{max}$(CHCl$_3$): 3360, 1775, 1750 cm$^{-1}$. Alternatively addition of p-toluene sulphonic acid to the crude amine dissolved in either provided the p-toluene sulphonic acid salt m.p. 163°–4°.

EXAMPLE 18

Benzyl 6α-(benzyloxycarbonylethyl)-6β-aminopenicillanate

Following the procedure of Example 17 benzyl 6α-benzylcarbonylethyl-6β-isocyanopenicillanate (2.54g) provided the title compound as a syrup. $\gamma_{max}$ (CHCl$_3$) 3350, 1770, 1740, 1600 cm$^{-1}$.

EXAMPLE 19

Benzyl 6α-(methylthio)-6β-aminopenicillanate

Benzyl 6α-methylthio-6β-isocyanopenicillanate (3.61g) was dissolved in chloroform (110mls) and treated with p-toluene sulphonic acid (1.9g). After 80 mins at 5° the solution was washed with aq. sodium bicarbonate, dried and evaporated. A solution of the residual free base in ether (150mls) on treatment with p-toluene sulphonic acid provided the crystalline p-toluene sulphonic acid salt (56%, m.p. 136°–8° dec). $\gamma_{max}$ (CHCl$_3$): 3200–3300 (b), 1785, 1740 cm$^{-1}$.

Phenylacetylation of benzyl 6α-(methylthio)-6β-aminopenicillanate using phenylacetyl chloride, followed by the chlorine-tritylamine-methanol procedure of Spitzer and Goodson (Tetrahedon Letters, [1973]273) produced benzyl 6α-methoxy phenylacetamidopenicillanate which was converted to 6α-methoxy phenyl-acetamidopenicillanic acid by catalytic hydrogenation.

We claim:

1. A compound of formula (VII):

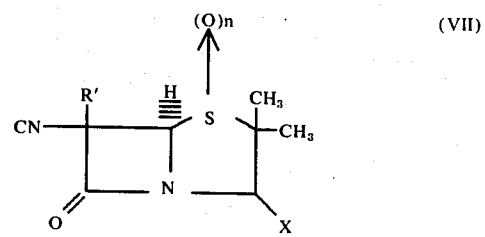

wherein n is zero or 1, X is a carboxylic acid group, or a non-toxic salt; or a conventional carboxylic acid ester readily hydrolysable to the parent acid, and R' is alkylthio.

2. A compound as claimed in claim 1 wherein n is zero.

3. A compound as claimed in claim 1 wherein X is a conventionally esterified carboxylic acid group.

4. A compound as claimed in claim 3 wherein X is a benzyl, phthalidyl or t-butyl ester.

5. A compound as claimed in claim 1 which is benzyl 6α-methylthio-6β-isocyanopenicillanate.

* * * * *